United States Patent [19]
Wynn

[11] Patent Number: 5,009,794
[45] Date of Patent: Apr. 23, 1991

[54] SYSTEM AND METHOD FOR CONTROLLING BUTTERFAT CONTENT IN STANDARDIZED MILK PRODUCT

[75] Inventor: William H. Wynn, San Carlos, Calif.

[73] Assignee: Wedgewood Technology, Inc., San Carlos, Calif.

[21] Appl. No.: 352,259

[22] Filed: May 16, 1989

[51] Int. Cl.$^5$ .................................................. A23C 9/00
[52] U.S. Cl. ................................... 210/739; 99/452; 137/93; 210/96.1; 210/745; 356/436; 426/231; 426/491; 364/176
[58] Field of Search .................... 99/452, 456; 210/94, 210/96.1, 514, 745, 790, 739, 85; 356/36, 436; 426/231, 491, 586; 364/160, 164, 176; 137/88, 89, 93

[56] References Cited

U.S. PATENT DOCUMENTS

| | | | |
|---|---|---|---|
| 2,752,815 | 7/1956 | Batchelor | 356/36 |
| 3,932,040 | 1/1976 | Warncke | 356/436 |
| 4,017,643 | 4/1977 | Lester | 426/231 |
| 4,144,804 | 3/1979 | O'Keefe et al. | 99/452 |
| 4,145,450 | 3/1979 | Winder et al. | 426/231 |
| 4,330,828 | 5/1982 | Smith et al. | 364/176 |
| 4,544,274 | 10/1985 | Cremers et al. | 356/436 |

FOREIGN PATENT DOCUMENTS

| | | | |
|---|---|---|---|
| 3238462 | 4/1984 | Fed. Rep. of Germany | 99/452 |
| 0552935 | 4/1977 | U.S.S.R. | 426/231 |
| 0562298 | 8/1977 | U.S.S.R. | 210/96.1 |
| 0567462 | 8/1977 | U.S.S.R. | 210/96.1 |
| 0760912 | 9/1980 | U.S.S.R. | 99/452 |
| 1318862 | 6/1987 | U.S.S.R. | 356/436 |

Primary Examiner—Robert A. Dawson
Assistant Examiner—Joseph Drodge
Attorney, Agent, or Firm—Flehr, Hohbach, Test, Albritton & Herbert

[57] ABSTRACT

System and method for controlling the content of a fluid product such as milk. The entire product stream is monitored continuously with an optical density meter, and the a signal corresponding to actual content of the stream is compared with the desired content. A correction signal which varies in accordance with the difference between the actual content signal and the desired content signal is provided, and the content of the product is adjusted in response to the correction signal by an amount which decreases as the content approaches the desired level.

21 Claims, 1 Drawing Sheet

SYSTEM AND METHOD FOR CONTROLLING BUTTERFAT CONTENT IN STANDARDIZED MILK PRODUCT

This invention pertains generally to the standardization of a fluid product having constituent parts and, more particularly, to a system and method for controlling the butterfat content of milk.

Raw milk contains a relatively large amount of butterfat in the form of cream, and the amount of cream varies with a number of factors such as the cows which give the milk, the feed eaten by the cows, and the season of the year.

In order to produce a milk product having a more uniform butterfat content, the raw milk is separated into low fat milk, or skim milk, and high fat milk, or cream. A portion of the high fat milk is then recombined with the low fat milk to provide a milk product having the desired fat content, e.g., 3%. The excess cream is drawn from the system and can be packaged separately or utilized in a milk product such as "half and half" or butter.

In processing milk in this manner, it is important to control the butterfat content accurately since that is what generally determines the food value and price of the product, as well as compliance with state and federal regulations. In the past, a number of techniques have been employed with varying degrees of success to control the butterfat content.

In some systems, which can be thought of as "feed forward" systems, the amount of cream to be added to the skim milk is, in effect, calculated from factors such as the flow volumes of the raw milk input, the flow volumes of the skim milk or cream, and the fat content of the skim milk or cream. There is generally no provision in these systems for actually monitoring the fat content of the resulting product. Examples of such systems are found in U.S. Pat. Nos. 3,829,584, 3,946,113, 3,983,257, 4,075,355, U.K. patent 1,435,984, Dutch Patent 7,407,130 (Which corresponds to U.S. Pat. No. 3,983,257) and Soviet Patent 552,935.

In another type of system, which is sometimes referred to as a "feedback" system, samples of the product are taken from the output stream, and the amount of cream introduced into the product stream is adjusted to maintain a desired butterfat content in the output stream. Examples of this type of system are found in U.S. Pat. Nos. 4,017,643, 4,074,622, 4,144,804 and 4,145,450.

U.S. Pat. No. 2,752,815 discloses a system in which butterfat content is monitored with an optical sensor and displayed by a meter. An optical sensor is also employed in the system shown in U.S. Pat. No. 4,144,804.

It is in general an object of the invention to provide an new and improved system and method for controlling the content of a fluid product such as milk.

Another object of the invention is to provide a system and method of the above character which overcome the limitations and disadvantages of techniques heretofore employed.

Another object of the invention is to provide a system and method of the above character in which the butterfat content of a standardized milk product is more accurately controlled than in systems of the prior art.

These and other objects are achieved in accordance with the invention by providing a reference signal corresponding to a desired content in a product stream, monitoring the product stream and providing a signal corresponding to the actual content of the product, monitoring the reference signal and the actual content signal and providing a correction signal which varies in accordance with the difference between the actual content and the desired content, and adjusting the content of the product in response to the correction signal by an amount which decreases as the content of the product approaches the desired content.

Figure 1:
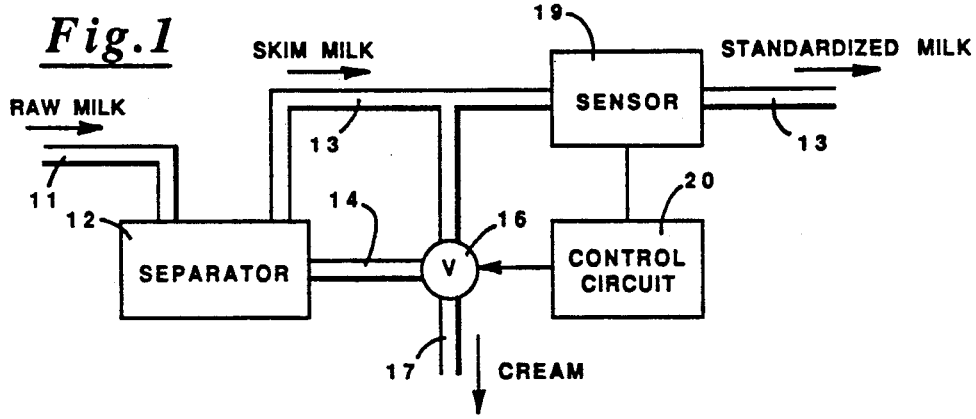
FIG. 1 is a schematic diagram of one embodiment of a system for producing milk having a standardized butterfat content in accordance with the invention.

As illustrated in FIG. 1, raw milk is applied to the input line 11 of a centrifugal separator 12 where it is separated into low fat, or skim, milk and high fat milk, or cream. The low fat milk is delivered to a product output line 13, and the high fat milk is delivered to a cream line 14. A cream control valve 16 has an inlet connected to cream line 14 and outlets connected to product output line 13 and to a cream output line 17. The adjustment of this valve controls the amount of high fat milk, or cream, which is combined with the low fat milk in the product output line, with the portion of the cream which is not delivered to the product output line being discharged through the cream output line.

The product output line passes through an in-line sensor 19 which monitors the butterfat content in the product stream. In one presently preferred embodiment, the sensor is an optical density sensor, and the entire product stream is monitored as it passes through the sensor. Suitable sensors are available from Wedgewood Technology, Inc., San Carlos, Calif., and include Model Nos. AF10-10-TC, AF10-20-TC, and AF10-30-TC. These sensors have stainless steel bodies and housings, with Pyrex windows, and they mount directly on the product output lines and operate at full flow and pressure. They monitor the optical density of the product stream which varies with the butterfat content of the milk. The Wedgewood sensors are particularly suitable since they can resolve small changes in the butterfat content, for example, a change of only 0.005% in a product having a 2% butterfat content.

A control circuit 20 monitors the output signal from sensor 19 and controls the operation of valve 16 to maintain a desired butterfat content in the product stream.

Figure 2:
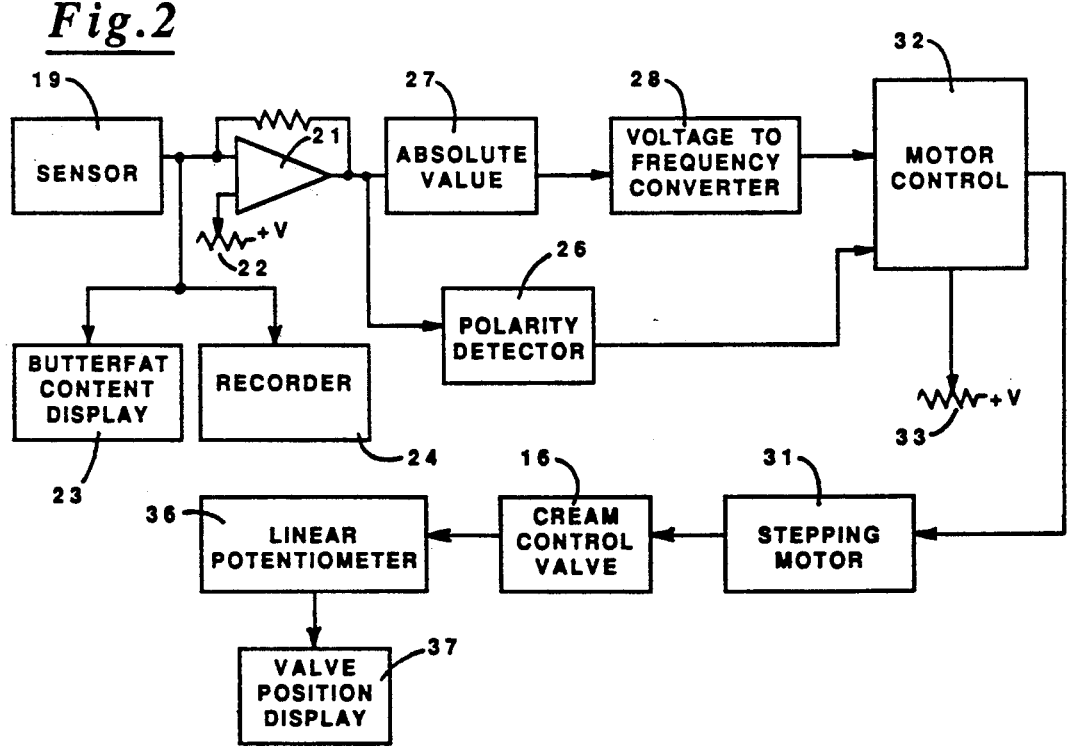
FIG. 2 is a block diagram of the control circuit employed in the embodiment of FIG. 1.

As illustrated in FIG. 2, the output of sensor 19 is connected to one input of a differential amplifier 21, and a reference signal corresponding to the desired butterfat content in the product stream is applied to a second input of this amplifier. The reference signal is provided by a manually adjustable potentiometer 22 connected to a voltage source +V, which permits an operator to set the desired butterfat content. The potentiometer can be provided with a dial (not shown) calibrated in units of butterfat content, e.g. percent, and by setting the potentiometer to the desired butterfat content, the operator sets the level of the reference signal.

The output of sensor 19 is also applied to a digital display 23, which displays the butterfat content of the product stream, and to a recorder 24. Any suitable type of recorder can be employed, and one particularly suitable type of recorder for this purpose is a circular recorder having a chart speed which can be adjusted from 1 to 168 hours per revolution.

The output of differential amplifier 21 is an error signal which consists of a voltage having an amplitude and polarity corresponding to the relative levels of the sensor signal and the reference signal. In one presently preferred embodiment, the sensor signal is a positive voltage having a magnitude which varies between zero and 5 volts, depending on the butterfat content of the milk and the sensitivity or range for which the system is set, and the reference voltage is set midway between the limits of the sensor voltage, e.g., at about 2.5 volts. If the sensor voltage is higher than the reference signal, the error signal is positive, and if the sensor voltage is lower than the reference voltage, the error signal is negative.

The output of amplifier 21 is connected to the inputs of a polarity detector 26 and a circuit 27 which delivers an output voltage corresponding to the absolute value of the error signal. The output of circuit 27 is connected to the input of a voltage to frequency converter 28 which produces an output signal containing a series of pulses which occur at a rate corresponding to the magnitude of the error signal, i.e. to the difference between the monitored butterfat content and the desired content.

Control valve 16 is driven by a stepping motor 31, and the signals from converter 28 and polarity detector 26 are applied to the inputs of a motor controller 32 which drives the stepping motor. The stepping motor thus advances one step in response to each pulse in the control signal from converter 28, and as the butterfat content of the product approaches the desired level, the pulse rate and, hence, the rate at which the valve is adjusted decreases, and the butterfat content approaches the desired level smoothly and gradually without overshoot or hunting. A manually adjustable potentiometer 33 connected to motor controller 32 permits the control valve to be set manually.

A linear potentiometer 36 is operatively connected to the control valve to provide a signal corresponding to the position of the valve. This signal is applied to a display 37 which indicates the position of the valve. This display is helpful to the operator in making certain that the system is set to operate within its normal range.

Operation and use of the system, and therein the method of the invention, can now be described. Potentiometer 22 is set for the desired butterfat content, and the system is turned on to begin processing the raw milk. As the raw milk is separated into low fat milk and high fat milk and a portion of the high fat milk is recombined with the low fat milk in product output line 13, the butterfat content in the product stream is monitored by sensor 19.

Sensor 19 provides an electrical signal which has a magnitude corresponding to the butterfat content, and this signal is compared with the reference signal from potentiometer 22 in differential amplifier 21. The signal produced by this amplifier has a magnitude and a polarity corresponding to the difference between the actual butterfat content in the product stream and the desired content.

Circuit 27 provides an output voltage corresponding to the absolute value, i.e. magnitude, of the error signal from differential amplifier 21, and polarity detector 26 provides a signal which indicates the polarity of the error signal. The absolute value signal from circuit 27 is converted to a pulse train or series of pulses by voltage to frequency converter 28. The pulses occur at a rate proportional to the magnitude of the error signal, i.e. to the difference between the actual butterfat content and the desired content.

The pulse signal from converter 32 and the polarity signal from detector 26 are applied to motor controller 32 which causes the stepping motor 31 to advance one step in response to each pulse in the pulse train and in the direction specified by the polarity signal. Each time the stepping motor steps, it adjusts the cream control valve by a fixed increment to increase or decrease the amount of high fat milk delivered to the product output line. When the monitored butterfat content differs by a larger amount from the desired fat content, the pulses occur at a higher rate, and the amount of cream added is increased or decreased more rapidly than it is when the content approaches the desired level. As the content gets closer to the desired level, the pulses occur less frequently, and the adjustment in the amount of cream added is made gradually and smoothly without overshoot or hunting about the desired level.

Visual indications of the butterfat content of the product stream and the position of the cream control valve 16 are provided by displays 23 and 37, and the butterfat content is recorded continuously by recorder 24.

The invention has a number of important features and advantages. The system is extremely easy to use, and it is also extremely accurate. The butterfat content in the product stream can be set simply by adjusting potentiometer 22, and thereafter the system will automatically adjust the fat content to this level and maintain it there. The system approaches the setpoint gradually, with the rate of adjustment decreasing as the desired level gets closer. This provides a smooth adjustment and effectively eliminates overshoot and hunting about the setpoint. By using an optical density sensor and monitoring the entire product output stream, a substantially greater accuracy is obtained than in systems in which only a portion of the product is monitored. This system can, for example, maintain an accuracy of 0.005% with a butterfat content of 2%. The system is easily installed in existing milk processing systems, and the control panel can be located remotely of the processing system, e.g. up to several hundred feet away.

The invention does not require any of the metering pumps or proportional control valving found in many prior art systems, and it operates on an on-line basis, providing very fast, essentially real time, control.

While the invention has been described with specific reference to a system and method for controlling the butterfat content in milk, it is applicable to other products as well, including fruit juice, beer and other fluid products having separable constituents.

It is apparent from the foregoing that a new and improved system and method have been provided for controlling the content of a fluid product such as milk. While only certain presently preferred embodiments have been described in detail, as will be apparent to those familiar with the art, certain changes and modifications can be made without departing from the scope of the invention as defined by the following claims.

I claim:

1. In a system for controlling fat content in a standardized milk product stream produced by combining high fat milk and low fat milk: mans for providing a reference signal corresponding to a desired fat content, a monitoring station including a sensor for continuously monitoring the entire product stream as it moves past the monitoring station and providing a sensor signal corresponding to the fat content of the milk in the product stream, means responsive to the reference signal and the sensor signal for providing a correction signal containing pulses occurring at a rate which decreases as the difference between the fat content of the product stream and the desired fat content decreases, and means responsive to the pulses in the correction signal for adjusting the relative amounts of high fat milk and low fat milk which are combined to produce the product stream at a rate which decreases as the fat content of the product stream approaches the desired fat content.

2. The system of claim 1 wherein the monitoring station sensor is an optical density sensor.

3. In a system for controlling fat content in a standardized milk product produced by combining high fat milk and low fat milk: means for setting a desired fat content in the milk product and providing a reference signal corresponding thereto, an optical density sensor for continuously monitoring the milk product and providing a sensor signal corresponding to the actual fat content in said product, means responsive to the reference signal and the sensor signal for providing an error voltage having a magnitude corresponding to the difference between the actual fat content and the desired fat content, and means including a voltage to frequency converter responsive to the error voltage for providing a control signal containing pulses occurring at a rate which varies in accordance with the difference between the actual fat content and the desired fat content, a control valve for adjusting relative amounts of high fat milk and low fat milk which are combined to produce the standardized product, and a stepping motor driven by the correction signal and operatively connected to the control valve for adjusting the control valve by one step in response to each pulse in the control signal.

4. The system of claim 3 including means including a linear potentiometer operatively connected to the control valve for monitoring the position of said valve.

5. The system of claim 3 wherein the means for setting the desired fat content comprises a potentiometer.

6. The system of claim 3 including means responsive to the sensor signal for visually indicating the fat content of the milk product.

7. The system of claim 3 including means responsive to the sensor signal for recording the fat content of the milk product.

8. In a system for producing a standardized milk product having a controlled butterfat content from a stream of raw milk: means for separating the raw milk into low fat milk and high fat milk, means for delivering the low fat milk to a product output line, valve means connected to the product line for introducing a portion of the high fat milk into the product line for combination in said line with the low fat milk to produce the standardized milk product, means for providing a reference signal corresponding to a desired amount of butterfat content in the standardized milk product, a monitoring station including an optical sensor for continuously monitoring the entire quantity of product in the line and providing a sensor signal corresponding to the butterfat content of the product, means responsive to the reference signal and the sensor signal for providing a correction signal which varies in accordance with the difference between the butterfat content of the product and the desired butterfat content, and means operatively connected to the valve means and responsive to the correction signal for actuating the valve means to adjust the butterfat content of the product at a rate which decreases as the butterfat content approaches the desired amount.

9. The system of claim 8 wherein the correction signal contains a series of pulses which occur at a rate corresponding to the difference between the butterfat content of the product and the desired content, and the means for actuating the valve means includes a stepping motor which moves one step in response to each pulse in the correction signal.

10. In a system for controlling the butterfat content of a standardized milk product: a source of low fat milk, a source of high fat milk, a product output line, valve means for controlling the relative amounts of low fat milk and high fat milk delivered from the sources to the output line, means for providing a reference signal corresponding to a desired butterfat content, means for monitoring the milk product in the output line and providing a signal corresponding to the actual butterfat content of the milk product in the output line, means responsive to the reference signal and the actual content signal for providing a correction signal which varies in accordance with the difference between the actual butterfat content and the desired butterfat content, and means responsive to the correction signal for actuating the valve means to adjust the butterfat content of the milk product in the output line at a rate which decreases as the butterfat content of the milk product approaches the desired butterfat content.

11. The system of claim 10 wherein the means for providing the correction signal includes means for providing pulses which occur at a rate corresponding to the difference between the actual content and the desired content, and the means for adjusting the content of the product includes a stepping motor which moves one step in response to each pulse in the correction signal.

12. In a method of controlling fat content in a standardized milk product stream produced by combining high fat milk and low fat milk, the steps of: providing a reference signal corresponding to a desired fat content, continuously monitoring the entire product stream as it moves past a monitoring station and providing a signal corresponding to the fat content of the milk in the product stream, monitoring the fat content signal and the reference signal to provide a correction signal containing pulses occurring at a rate which varies with the difference between the fat content of the product stream and the desired fat content, and adjusting the relative amounts of high fat milk and low fat milk which are combined to produce the product stream by an incremental step in response to each pulse in the correction signal.

13. The method of claim 12 wherein the product stream is monitored with an optical density sensor.

14. In a method of controlling fat content in a standardized milk product produced by combining high fat milk and low fat milk, the steps of: setting a desired fat content for the milk product and providing a reference signal corresponding thereto, continuously monitoring the milk product with an optical density sensor and providing a signal corresponding to the actual fat content in said product, monitoring the reference signal and the sensor signal to provide an error voltage having a magnitude which decreases as the difference between the actual fat content and the desired fat content decreases, applying the error signal to a voltage to frequency converter to produce a control signal containing pulses occurring at a rate which as the difference between the actual fat content and the desired fat content decreases, advancing a stepping motor by one step on response to each pulse in the control signal, and driving a control valve with the stepping motor to adjust the relative amounts of high fat milk and low fat milk which are combined to produce the standardized product at a rate which decreases as the actual fat content approaches the desired fat content.

15. The method of claim 14 including the step of monitoring the position of the control valve with a linear potentiometer operatively connected to the valve.

16. The system of claim 14 including the step of visually indicating the fat content of the milk product in response to the sensor signal.

17. The method of claim 14 including the step of recording the fat content of the milk product in response to the sensor signal.

18. In a method of producing a standardized milk product having a controlled butterfat content from a stream of raw milk, the steps of: separating the raw milk into low fat milk and high fat milk, delivering the low fat milk to a product output line, introducing a portion of the high fat milk into the product line through a control valve for combination in said line with the low fat milk to produce the standardized milk product, providing a reference signal corresponding to a desired amount of butterfat content in the standardized milk product, continuously monitoring the entire quantity of product in the line and providing a signal corresponding to the butterfat content of the product, monitoring the reference signal and the sensor signal and providing a correction signal which varies in accordance with the difference between the butterfat content of the product and the desired butterfat content, and actuating the control valve in response to the correction signal to adjust the butterfat content of the product at a rate which decreases as the butterfat content approaches the desired amount.

19. The method of claim 18 wherein the correction signal contains a series of pulses which occur at a rate corresponding to the difference between the butterfat content of the product and the desired content, and the correction signal is applied to a stepping motor which moves the control valve one step in response to each pulse in the correction signal.

20. In a method of controlling the butterfat content of a standardized milk product produced by combining low fat milk and high fat milk, the steps of: providing a reference signal corresponding to a desired butterfat content, monitoring the milk product and providing a signal corresponding to the actual butterfat content of the product, monitoring the reference signal and the actual butterfat content signal and providing a correction signal which varies in accordance with the difference between the actual butterfat content and the desired butterfat content, and adjusting the relative amounts of low fat milk and high fat milk delivered to the milk product in response to the correction signal at a rate which decreases as the butterfat content of the milk product approaches the desired butterfat content.

21. The method of claim 20 wherein the correction signal contains a series of pulses which occur at a rate corresponding to the difference between the actual content and the desired content, and the pulses are applied to a stepping motor which moves one step in response to each pulse in the correction signal to adjust the content of the product.

* * * * *